United States Patent [19]

Pavani

[11] Patent Number: 5,273,916
[45] Date of Patent: Dec. 28, 1993

[54] USE OF 1,2-DIPALMITOYL-L-α-PHOSPHATIDYL-N,N-DIMETHYLETHANOLAMINE IN DERMATOLOGIC COMPOSITIONS

[75] Inventor: Pier G. Pavani, Rastignano Pianoro, Italy

[73] Assignees: Mivett Nuovi Laboratori Di P. G. Pavani; C S.N.C., Bologna, Italy

[21] Appl. No.: 946,751

[22] Filed: Sep. 17, 1992

[30] Foreign Application Priority Data

Sep. 18, 1991 [IT] Italy .................. MI91 A 002466

[51] Int. Cl.$^5$ ............................................. A61K 31/66
[52] U.S. Cl. ................................................ 514/114
[58] Field of Search ....................................... 514/114

[56] References Cited

U.S. PATENT DOCUMENTS 4,877,805 10/1989 Kligman .................. 514/381

Primary Examiner—Leonard Schenkman
Attorney, Agent, or Firm—Bucknam and Archer

[57] ABSTRACT

The use of 1,2-dipalmitoyl-L-α-phosphatidyl-N,N-dimethylethanolamine for the manufacturing of dermatological and cosmetic compositions for antiageing and cutaneous microcirculation treatment.

5 Claims, No Drawings

USE OF 1,2-DIPALMITOYL-L-α-PHOSPHATIDYL-N,N-DIMETHYLETHANOLAMINE IN DERMATOLOGIC COMPOSITIONS

The present invention relates to the use of 1,2-dipalmitoyl-L-α-phosphatidyl-N,N-dimethylethanolamine for the manufacturing of dermatologic compositions useful for the treatment of cutaneous microcirculation. Particularly, it is a further object of the present invention the use of the above mentioned compound for the manufacturing of dermatologic compositions having antiageing activity.

Skin ageing is mainly due to fibroblast ageing, which is a derm component, where it synthesises collagen and elastic fibers, several macromolecular substances such as proteoglycans, proteins as fibronectin, elastin, laminin, etc.; the fibroblast is further indirectly responsible for the activity of all the epidermal cells.

The fibroblast is immersed in the fundamental substance wherein the other cells, such as macrophages and mast cells, resides. Macrophages include and destroy substances which are toxic to the skin, such as certain bacteria and viruses, for example.

The old fibroblast produces the above mentioned substances in an extremely reduced amount. Said substances are very important in order to maintain the skin young; therefore problems such as dryness, dehydration, opacity arise, in other words all the most disagreeable phenomena of the ageing skin.

Skin antiageing treatment has not only an aesthetic or cosmetic meaning, but also a more general dermatological meaning, since antiageing compounds act also on several skin components, i.e., defensive elements, vascular district, structural elements, etc.

The use of retinoic acid (US Patent 4,603,146) and azelaic acid (EP-A-0336880) is well known in antiageing treatment. Said compounds are toxic above certain doses, both in single (acute toxicity) and prolonged (chronic toxicity) administrations.

It has now been found that 1,2-dipalmitoyl-L-α-phosphatidyl-N,N-dimethylethanolamine develops a surprising dermatological activity, acting both on the cutaneous microcirculation and on the defensive mechanisms of the derm, leading particularly to an antiageing activity.

1,2-Dipalmitoyl-L-α-phosphatidyl-N,N-dimethylethanolamine is a phospholipid which is a component of the pulmonary surfactant. Pulmonary surfactant is a complex mixture formed by simple sugars and phospholipids (E. Scarpelli, Il sistema surfactant del polmone, Casa Editrice Ambrosiana, Milano 1972).

Pulmonary surfactant allows the oxygen to pass into the blood, and it further activates the macrophages in the pulmonary alveolus. Said macrophages maintain the pulmonary alveolus cavity clean, clearing it from atmospheric dust and from old cell fragments which have fallen into the alveolar cavity.

Recent researches proved that treating the skin with fractions of pulmonary surfactant containing phospholipid mixtures the following phenomenon occurs: the fractions interpenetrate with the membranes of the cells which are present in the derm and analogously to what determined in the pulmonary alveolus, activate the macrophages, which, in this case, phagocytize and destroy the old fibroblasts. Accordingly, young fibroblasts proliferate, and subsequently produce the precursors of the typical elements of the derm in great quantity; collagen fibers, elastic fibers, proteoglycanes, fibronectin, etc.

During a study for the identification of pulmonary surfactant fractions, it has been found that 1,2-dipalmitoyl-L-α-phosphatidyl-N,N-dimethylethanolamine surprisingly stimulates the cutaneous macrophages, thus contributing to the antiageing activity.

The present invention is advantageous because it provides a single active ingredient, which is therefore precisely dosable to obtain compositions with constant activity, without the necessity of using complex extracts of animal origin, whose composition is not always constant.

Further, 1,2-dipalmitoyl-L-α-phosphatidyl-N,N-dimethylethanolamine is commercially available in high purity (Sigma product number P0399, P1634; Fluka 52552).

Besides performing antiageing activity by the elimination mechanism of the old fibroblast, 1,2-dipalmitoyl-L-α-phosphatidyl-N,N-dimethylethanolamine is also active on the cutaneous microcirculation.

The antiageing, hydrating and elasticizing activities of the compound of the invention were demonstrated during a clinical and instrumental evaluation of the skin treated before and after one month's product use.

10 Healthy female volunteers, ageing from 30 to 35, were examined after dermatological control.

The subjects were asked to interrupt any other cosmetic treatment and to start the test having their skin cleansed from make up and other creams from two hours at least.

Method

On the zygomatic region of the selected subjects the following parameters were evaluated: pH, surface lipids, hydration, mechanic properties, surface microwrinkle profile.

The evaluations were done in conditioned environment at room temperature (22° C.) and constant relative humidity (40%) after 15'acclimatization.

The following instruments were used for the measurements:

pH meter pH 90 Schwarzhaupt Medizintechnik (Germany)
Corneometer CM 820 Courage-Khazaka Koln (Germany)
Sebumeter SM 810 Courage-Khazaka Koln (Germany)
Cutometer SEM 474 Courage-Khazaka Koln (Germany)
Skin Image Analyzer Dermatec Paris (France)

Results

| Subjects 10 | pH mean | standard deviation | MSE |
|---|---|---|---|
| before | 5.6 | 0.29 | 0.09 |
| after | 5.69 | 0.39 | 0.12 |
| Student's T test | | | $p > 0.05$ |

No significant variations were observed during the treatment.

| Subjects | Surface lipids | | |
|---|---|---|---|
| 10 | mean | standard deviation | MSE |
| before | 53.9 | 27.46 | 8.68 |
| after | 61.5 | 28.23 | 8.93 |
| Student's T test | | | p > 0.05 |

No significant variations were observed during the treatment.

| Subjects | Hydration | | |
|---|---|---|---|
| 10 | mean | standard deviation | MSE |
| before | 61.8 | 8.3 | 2.62 |
| after | 72.5 | 6.79 | 2.15 |
| Student's T test | | | p < 0.05 |

After one-month's use of the product, a sharp increase of hydration occurred.

| Subjects | Elastometry Percent elasticity | | |
|---|---|---|---|
| 10 | mean | standard deviation | MSE |
| before | 43.09 | 13.48 | 4.26 |
| after | 51.56 | 11.09 | 3.51 |
| Wilcoxon's rank sum test | | W = −35.0 | p < 0.06 |

A significant increase of per cent elasticity was registered, the increase was determined by the tensile stretch.

| Index | | Profilometry | | |
|---|---|---|---|---|
| | | mean | standard dev. | significance |
| RA | before | 5.92 | 0.84 | |
| | after | 5.35 | 0.51 | p < 0.06 |
| S | before | 10,866.15 | 10.07 | |
| | after | 10,870.18 | 33.67 | p > 0.06 |
| RT | before | 29.8 | 4.83 | |
| | after | 26.7 | 3.34 | p > 0.06 |
| RZ | before | 21.74 | 3.75 | |
| | after | 20.32 | 2.52 | p > 0.06 |
| RN | before | 10 | 3.83 | |
| | after | 8.5 | 2.95 | p > 0.06 |

Legend:
RA: mean roughness
S: length of the curve
RT: deviation between peak and valley
RZ: mean amplitude
RN: peak number
Mean values were analyzed with Wilcoxon's rank sum test.
A significant reduction of mean roughness was evidenced.

The compound of the invention does not modify the surface acid mantle. During the observation period the surface lipids showed no increase, whereas a significant increase of hydration level and an improvement of percent elasticity were observed. As to surface profile, all the indexes improved (S remaining unchanged), particularly with respect to the mean roughness, which modified in a statistically significant manner.

The present invention is preferably applied in ophthalmology, particularly in the treatment of unaestheticisms due to the alteration of palpebral microcirculation, such as wrinkles, crow's feet, swellings, ring under the eyes.

The effect of 1,2-dipalmitoyl-L-α-phosphatidyl-N,N-dimethylethanolamine on the palpebral microcirculation was proved during a study carried out on volunteers, aged from 40 to 70, and bearing evident signs of palpebral swelling, rings under the eyes and wrinkles in their periocular region.

The observation of palpebrae microcirculation was carried out by means of radiography after injecting a contrast medium in the palpebral branch of the opthalmic artery.

Further, an ultrastructural investigation on the derm of a cutis fragment, having 1 millimiter maximum size, taken from a region facing the palpebral commissure, was carried out. The cutis fragment was fixed in 2.5% glutaric aldehyde in phosphate buffer and subsequently treated with the usual techniques for electronic microscope observation.

Over the above described operation, a thermographic measurement on the cutis of the palpebral region was made. In every case the observations were carried out before and after the application of 1,2-dipalmitoyl-L-α-phosphatidyl-N,N-dimethylethanolamine, which was carried with lanoline. Said application was done dayly for 3 weeks with a 30 seconds' massage on the palpebral cutis.

The control was done on subjects treated with carrier only.

The arteriography allows to put in evidence the fine vascularization of the eyelids. Before the treatment, deep vascular branches are partially visible and show irregular flow often interrupted by radiotransparent spaces. The surface vascular network appears to be formed by a very thick interlacement of vessels, particularly extended near the palpebral fissure. After the treatment, deep vascular branches are well visible and constitute a thick network spreading through almost the whole eyelid thickness. Surface vascular branches form a sort of dense felt extending throughout the palpebral fissure.

Ultrastructural images show that in the palpebral fissure of the untreated subjects and lanoline treated subjects, fibroblasts have poor synthetic activity. In fact, their cytoplasm is poor in organella and rough reticulum is scarce, secretion vesicles being almost absent. The surrounding matrix is crossed by many collagen fibrils and shows a remarkable lack of glycosaminoglicans which are evidenced in the form of downy filaments.

In the palpebral derm of the treated subjects, many macrophages were observed, these being in evident phagocytary activity, as the abundant lysosomes in their cytoplasm proved. Fibroblasts show a particularly developed rough reticulus and many secretion granules, which demonstrate a remarkable synthetic activity. The matrix of perivascular spaces appears litterally full of glycosaminoglycans, which form filaments differently arranged.

Thermography, which was performed before the treatment, showed extended dysthermic and hypothermic regions, as shown by green, blue and pomace colours.

After the treatment a normalization of the temperature over all the eyelid region was observed, as indicated by blue colour.

The treatment induces fibroblast proliferation and subsequent increase of their synthetic activity. This phenomenon involves an accumulation of glycosaminoglycans in the perivascular matrix. Said matrix, as result of the accumulation of glycosaminoglycans, enriches wit water and in such a way facilitates arteriolar pulsatility. From this an improvement of all the microcirculation and a mitigation of the above mentioned unaesthetisms come out.

According to the obtained results, the use of 1,2-dipalmitoyl-L-α-phosphatidyl-N,N-dimethylethanolamine, can be foreseen to exert beneficial effect even in the treatment of peripheral vascular disorders such as haemorrhoids, varicose veins, couperose, etc.

Dermatological compositions containing 1,2-dipalmitoyl-L-α-phosphatidyl-N,N-dimethylethanolamine, optionally combined with other active ingredients, are a further object of the invention. Said compositions may be prepared according to well-known techniques, such as, for example, those described in "Remington's Pharmaceutical Sciences Handbook" Mack Pub. Co., USA. Examples of compositions are creams, gels, milk, lotion, ointment, lipsticks, emulsions, liposomal formulations and the like.

1,2-Dipalmitoyl-L-α-phosphatidyl-N,N-dimethylethanolamine is contained in dosages ranging from 0.0001% to 0.01%, preferably 0.001%.

The following examples further illustrate the invention.

EXAMPLE 1

| Antiageing gel for eye contour | |
|---|---|
| Cellosize Peg 10 (Cellosize Peg 10 is a hydroxyethylcellulose) | 0.35% |
| 1,2 dipalmitoyl-L-α-phosphatidyl-N,N-dimethylethanolamine | 0.001% |
| 5% Horse-chestnut liposome | 3.2% |
| NMF hydrating factor | 2% |
| Panthenol | 1% |
| Sorbitol 70% | 2% |
| Bidistilled glycerin | 1% |
| Blue dye | 0.05% |
| Perfume | 0.1% |
| Hamamelis distilled water | q.s. to 100 |
| Kathon OG (Katton is 2-octyl 3 (2H) isothiazolone) | 0.025% |
| Gram 1 | 0.1% |

, EXAMPLE 2

| Face antiageing hydrating cream | |
|---|---|
| D.I.I.C. 671400 Ammonium O.T.F.A. (and) Potassium Palmitoyl Hydrolyzed Animal Protein and "Cetearyl" alcohol and "Glycearyl" Stearate | 10% |
| Cetyl Stearyl Alcohol | 2% |
| Silicone oil 350 | 1% |
| Myritol 318 Henxel (Myritol is a caprylic/capric acid triglyceride) | 5% |
| Bidistilled Glycerin 30 bE | 5% |
| Hamamelis distilled water | q.s. to 100 |
| Kathon OG | 0.025% |
| Gram 1 | 0.1% |
| Panthenol | 1% |
| NMF hydrating factor | 3% |
| 5% Horse-chestnut liposome | 5% |
| 1,2-dipalmitoyl-L-α-phosphatidyl-N,N-dimethylethanolamine | 0.001% |
| Perfume | 0.1% |

EXAMPLE 3

| Anti-couperose cream | |
|---|---|
| D.I.I.C. 671400 Ammonium O.T.F.A. (and) Potassium Palmitoyl Hydrolyzed Animal Protein and "Cetearyl" alcohol and "Glycearyl" Stearate | 10% |
| Cetyl Stearyl Alcohol | 2% |
| Silicone oil 350 | 1% |
| Myritol 318 Henkel | 5% |
| Bidistilled Glycerin 30 bE | 5% |
| Hamamelis distilled water | q.s. to 100 |
| Kathon OG | 0.025% |
| Gram 1 | 0.1% |
| 5% Bilberry liposome | 4% |
| 5% Horse-chestnut liposome | 2% |
| 5% Butcher's broom liposome | 1% |
| 1,2-dipalmitoyl-L-α-phosphatidyl-N,N-dimethylethanolamine | 0.001% |

EXAMPLE 4

| Leg "anti-heaviness gel" adjuvant in varicose vein treatment | |
|---|---|
| Cellosize Peg 10 | 0.50% |
| 1,2-dipalmitoyl-L-α-phosphatidyl-N,N-dimethylethanolamine | 0.001% |
| 5% Horse-chestnut liposome | 5% |
| NMF hydrating factor MNF | 3% |
| Blue dye | 0.002% |
| Perfume | 0.1% |
| Hamamelis distilled water | q.s. to 100 |
| Kathon OG | 0.025% |
| Gram 1 | 0.1% |

EXAMPLE 5

| Leg "anti-heaviness" gel adjuvant in cellulitis treatment | |
|---|---|
| Cellosize Peg 10 | 0.50% |
| 1,2-dipalmitoyl-L-α-phosphatidyl-N,N-dimethylethanolamine | 0.001% |
| 5% Ivy liposome | 2% |
| 5% Horse-chestnut liposome | 3% |
| NMF hydrating factor | 3% |
| Blue dye | 0.05% |
| Perfume | 0.1% |
| Hamamelis distilled water | q.s. to 100 |
| Kathon OG | 0.025% |
| Gram 1 | 0.1% |

EXAMPLE 6

| Cream against strech marks | |
|---|---|
| D.I.I.C. 671400 Ammonium O.T.F.A. (and) Potassium Palmitoyl Hydrolyzed Animal Protein and "Cetearyl" alcohol and "Glycearyl" Stearate | 10% |
| Cetyl Stearyl Alcohol | 2% |
| Silicone oil 350 | 1% |
| Myritol 318 Henkel | 5% |
| Bidistilled Glycerin 30 bE | 5% |
| Distilled water | q.s. to 100 |
| Kathon OG | 0.025% |
| Gram 1 | 0.1% |
| 5% Ivy liposome | 1% |
| Horsetail glycolic extract | 1% |
| Catchweed glycolic extract | 2% |
| Lady's mantle glycolic extract | 1% |

| Cream against strech marks | |
| --- | --- |
| 1,2-dipalmitoyl-L-α-phosphatidyl-N,N-dimethylethanolamine | 0.001% |
| Perfume | 0.1% |

EXAMPLE 7

| Cream against cellulitis | |
| --- | --- |
| D.I.I.O. 671400 Ammonium O.T.F.A. (and) Potassium Palmitoyl Hydrolyzed Animal Protein and "Cetearyl" alcohol and "Glycearyl" Stearate | 10% |
| Cetyl Stearyl Alcohol | 2% |
| Silicone oil 350 | 1% |
| Myritol 318 Kenkel | 5% |
| Bidistilled Glycerin 30 bE | 5% |
| Hamamelis distilled water | q.s. to 100 |
| Kathon OG | 0.025% |
| Gram 1 | 0.1% |
| 5% Ivy liposome | 2% |
| 5% Horse-chestnut liposome | 3% |
| 1,2-dipalmitoyl-L-α-phosphatidyl-N,N-dimethylethanolamine | 0.001% |
| Perfume | 0.1% |

EXAMPLE 8

| Hair strenghthening lotion | |
| --- | --- |
| 1,2-dipalmitoyl-L-α-phosphatidyl-N,N-dimethylethanolamine | 0.005% |
| Trimetyl Xanthine | 0.3% |
| Panthenol | 0.25% |
| Nettle glycolic extract | 0.25% |
| Peg-15-Tallow-Polyamine | 1% |
| Rose distilled water | q.s. to 100 |
| Kathon OG | 0.025% |
| Gram 1 | 0.1% |

I claim:

1. The method of combating aging by stimulating cutaneous microcirculation and cutaneous macrophages, promoting hydration and elasticity of the skin of a human subject in need of treatment and treating varicose veins and couperose which consists of applying to the skin of said subject a composition in unit dosage form containing 1,2-dipalmitoyl-L-α-phosphatidyl-N, N-dimethylethanolamine in the amount between 0.0001% and 0.01%.

2. The method according to claim 1 wherein said composition is in the form of a gel, a cream, a lotion, an ointment, a lipstick, an emulsion, or a liposomal formulation.

3. The method of treatment of palpebral swelling, rings under the eyes and wrinkles in the periocular region which consists of applying to said periocular region and to the eyelids of a human subject in need of treatment a composition in unit dosage form containing 1,2-dipalmitoyl-L-α-phosphatidyl-N, N-dimethylethanolamine in the amount between 0.001% and 0.01%.

4. The method according to claim 3 which consists of applying to each periocular region and to the eyelids a gel containing 0.001% of 1,2-dipalmitoyl-L-α-phosphatidyl-N,N-dimethylethanolamine, 0.35% of hydroxyethylcellulose, 0.015% of 2-octyl-3-(2H) isothiazolone and 1% glycerin in addition to water and other inert excipients.

5. The method according to claim 2 wherein said composition contains inert excipients.

* * * * *